United States Patent [19]

Lantzsch et al.

[11] 4,276,225
[45] Jun. 30, 1981

[54] DECARBALKOXYLATION OF CARBOXYLIC ACID ESTERS

[75] Inventors: Reinhard Lantzsch, Cologne; Hellmut Hoffmann, Wuppertal, both of Fed. Rep. of Germany

[73] Assignee: Bayer Aktiengesellschaft, Leverkusen, Fed. Rep. of Germany

[21] Appl. No.: 822,967

[22] Filed: Aug. 8, 1977

[30] Foreign Application Priority Data

Aug. 26, 1976 [DE] Fed. Rep. of Germany ....... 2638453

[51] Int. Cl.³ ..................... C07C 67/32; C07C 45/65; C07C 120/00
[52] U.S. Cl. ....................................... 260/408; 560/1; 560/9; 560/18; 560/103; 560/105; 560/122; 560/123; 560/124; 560/128; 560/152; 560/174; 560/205; 560/219; 560/265; 260/410.9 R; 260/464; 260/465 R; 260/465 H; 260/465.1; 260/465.7; 260/465.8 R; 260/465.9; 568/314; 568/346; 569/392
[58] Field of Search ..................... 260/522, 405.5, 408, 260/410.9 R, 464, 465 R, 465 H, 465.1, 465.7, 465.8 R, 465.9; 562/506; 560/1, 9, 18, 103, 105, 122, 123, 124, 128, 152, 174, 205, 219, 265; 568/314, 346, 392

[56] References Cited

U.S. PATENT DOCUMENTS

| | | | |
|---|---|---|---|
| 2,663,737 | 12/1953 | McCormack | 260/606.5 P |
| 2,663,739 | 12/1953 | McCormack | 260/606.5 P |
| 3,816,524 | 6/1974 | Grinstead | 260/535 R |

FOREIGN PATENT DOCUMENTS 2536145 8/1975 Fed. Rep. of Germany .

OTHER PUBLICATIONS

Krapcho et al., "Decarboxylation of Geminal Diesters . . .", Tetrahedron Letters (1973) No. 12, pp. 957-960.

Krapcho et al., (above subject continued) Ibid (1974), No. 13, pp. 1091-1094.

Primary Examiner—Natalie Trousof
Assistant Examiner—L. Hendriksen
Attorney, Agent, or Firm—Sprung, Felfe, Horn, Lynch & Kramer

[57] ABSTRACT

A carboxylic acid ester activated in α-position by a keto, ester or nitrile group, i.e. of the formula

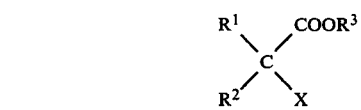

where X is COOR⁴, COR⁵ or CN, and the several R's can have various meanings but only R¹ and R² can be hydrogen, is decarbalkoxylated by heating in the presence of a salt, e.g. sodium chloride, and a phosphorus-containing solvent such as a pholine oxide, phospholane oxide or phosphetane oxide of the formulas

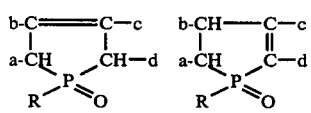

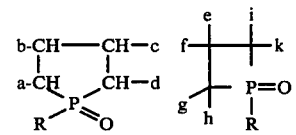

wherein a-k and R can have varied definitions.

Water is present either at the outset or end of the reaction before product separation. The reaction proceeds smoothly and in good yields.

8 Claims, No Drawings

DECARBALKOXYLATION OF CARBOXYLIC ACID ESTERS

The present invention relates to an unobvious process for the decarbalkoxylation of carboxylic acid esters which carry, in the α-position to the ester group, a further ester group, a keto group or a CN group.

The decarbalkoxylation of geminal diesters is usually carried out in several reaction steps (A, B and C):

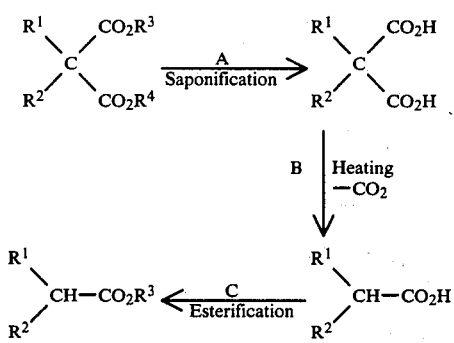

The radicals $R^1$–$R^4$ are defined hereinbelow.

Various substituted diesters cannnot be saponified, or can be saponified only with difficulty, in this manner. Thus, the reaction sequence A, B, C cannot be carried out if $R^1$ and $R^2$ form a cyclopropane ring, since it is not possible to decarboxylate the dicarboxylic acid (step B) while preserving the cyclopropane ring (Organikum (Organic Chemistry), VEB Deutscher Verlag der Wissenschaften, Berlin 1965, page 402).

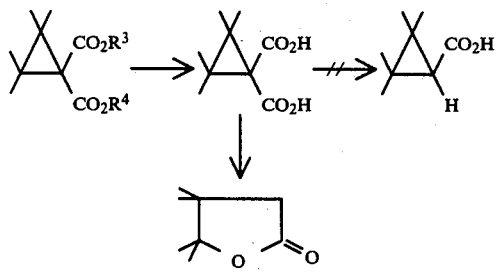

However, it has been disclosed to carry out the decarbalkoxylation of geminal diesters, as well as of β-ketoesters and α-cyanoesters, in a single stage by heating the geminal diester or ketoester or α-cyanoester in dimethylsulphoxide (DMSO) in the presence of water (Tetrahedron Letters 1973, page 957-960 and 1974, page 1,091-1,094). It is not necessary to add salts here (Tetrahedron Letters 1974, page 1,095-1,096).

However, the use of dimethylsulphoxide (DMSO) has serious disadvantages, so that this process cannot be used industrially.

A partial decomposition of DMSO takes place at the temperatures required; in addition, DMSO cannot be recovered from a DMSO/water mixture. However, in most cases the isolation of the decarbalkoxylated compound is carried out by pouring the reaction mixture into water and then extracting the decarbalkoxylated compound with one of the customary organic solvents. Only in very rare cases has the decarbalkoxylated compound such a low boiling point that it can be distilled out from the mixture directly.

A further serious disadvantage is that the conversion and yield are often extremely low. In many cases the conversion is only about 20% after a reaction time of 10 hours. This is also the case, for example, in a reaction which is important industrially and which is described in German Offenlegungsschrift (German Published Specification) No. 2,536,145:

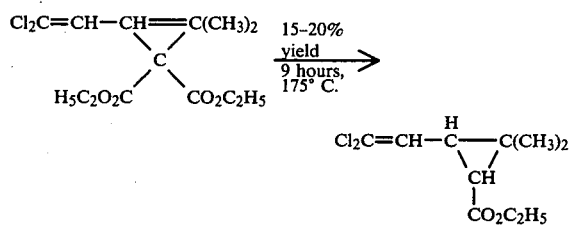

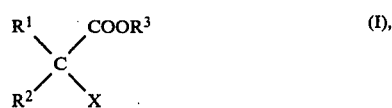

The present invention now provides a process whereby a carboxylic acid ester of the general formula

in which
X represents a radical $COOR^4$, $COR^5$ or CN,
$R^1$ and $R^2$, which may be identical or different, each represent hydrogen, alkyl, alkenyl, alkynyl, aryl or aralkyl, or, $R^1$ and $R^2$, together with the adjacent carbon atom, form a cycloaliphatic ring which is optionally substituted by CN, alkyl, alkenyl, aryl, aralkyl, alkylthio or arylthio, the substituents of the cycloaliphatic ring optionally being substituted by halogen,
$R^3$ and $R^4$, which may be identical or different, each represent alkyl and
$R^5$ represents alkyl, alkenyl, aryl or aralkyl, or
$R^4$ or $R^5$ can form a ring with $R^2$ and the intermediate atoms,
is decarbalkoxylated to a carboxylic acid ester of the general formula

in which $R^1$, $R^2$ and X have the meanings stated above, in which process the carboxylic acid ester of the general formula (I) is heated in the presence of a solvent containing phosphorus and in the presence of a salt of the general formula

KA       (III), in which
K represents an equivalent of a cation, and
A represents an equivalent of an anion, such as halide, $CN^-$, $SCN^-$ or $N_3^-$,
to a temperature of about 100° to 250° C.

Surprisingly, the decarbalkoxylation process according to the invention can proceed smoothly and with good yields. In addition, the solvent used can be recovered almost quantitatively. Thus the decarbalkoxylation process according to the invention can be carried out substantially more economically than the known processes.

Preferred carboxylic acid esters of the general formula (I) are those in which $R^1$ and $R^2$, which may be identical or different, each represent H, or a $C_1$–$C_{18}$-alkyl radical, a $C_2$–$C_{18}$-alkenyl radical, a $C_2$–$C_{18}$-alkynyl radical, a $C_6$–$C_{14}$-aryl radical or a $C_7$–$C_{20}$-aralkyl radical, each of which can optionally be substituted by halogen (namely F, Cl, Br or I) or cyano, or $R_1$ and $R_2$, together with the adjacent carbon atom, form a cycloaliphatic ring which contains 3–8 carbon atoms and optionally can be substituted by cyano or by $C_1$–$C_{18}$-alkyl, $C_2$–$C_{18}$-alkenyl, $C_6$–$C_{14}$-aryl, $C_7$–$C_{20}$-aralkyl, alkylthio or arylthio, any of which in turn can be substituted by halogen, (namely F, Cl, Br or I), $R^3$ represents a $C_1$–$C_4$-alkyl group, $R^4$ represents a $C_1$–$C_4$-alkyl group or, together with $R^2$, forms a lactone with 3–6 carbon atoms, and $R^5$ represents a $C_1$–$C_{18}$-alkyl group, a $C_2$–$C_{18}$-alkylene group, a $C_6$–$C_{14}$-aryl group or a $C_7$–$C_{20}$-aralkyl group, which can be substituted by halogen atoms, or $R^5$, together with $R^2$, forms a cyclic ketone with 3–7 carbon atoms.

Particularly preferred compounds of the formula (I) are those in which X represents $CO_2R^4$ and $R^1$ and $R^3$, together with the adjacent carbon atom, form an optionally substituted cyclopropane ring.

Particularly suitable carboxylic acid esters of the general formula (I) are: 2,2-dimethyl-3-(2',2'-difluorovinyl)-cyclopropane-1,1-dicarboxylic acid diethyl ester, 2,2-dimethyl-3-(2',2'-dichlorovinyl)-cyclopropane-1,1-dicarboxylic acid diethyl ester, 2,2-dimethyl-3-(2',2'-dibromovinyl)-cyclopropane-1,1-dicarboxylic acid diethyl ester, 2,2-dimethyl-3-methylthio-cyclopropane-1,1-dicarboxylic acid dimethyl ester, 3-cyano-2,2-dimethyl-cyclopropane-1,1-dicarboxylic acid diethyl ester, 2,2-dimethyl-3-phenylthiocyclopropane-1,1-dicarboxylic acid diethyl ester, 2,2-dimethyl-3-(2',2'-dichlorovinyl)-cyclobutane-1,1-dicarboxylic acid diethyl ester, 2,2-dimethyl-3-propionyl-malonic acid diethyl ester, 2,2-dimethyl-3-propenyl-malonic acid diethyl ester, diisopropyl-malonic acid diethyl ester, isopropyldichloropropenyl-malonic acid diethyl ester, diisopropylcyanoacetic acid ethyl ester and isopropyldichloropropenylcyanoacetic acid ethyl ester.

The phosphorus-containing solvents that can be used in carrying out the process according to the invention are known (see U.S. Pat. Nos. 2,663,737 and 2,663,739). They are, in general, phospholine oxides, phospholane oxides or phosphetane oxides of the general formulae:

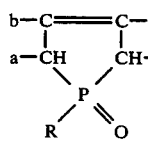

(IV)

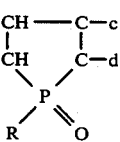

(V)

-continued

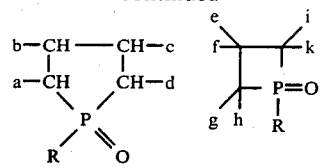

(VI)    (VII)

wherein a, b, c and d, which may be identical or different, each represent H, alkyl, alkenyl, aryl, aralkyl, alkoxy, Cl or Br or represent a tetramethylene group which, together with two adjacent carbon atoms of the heterocyclic ring, forms a cycloaliphatic ring, provided that if a, b, c and d are aliphatic, they contain a total of not more than 6 carbon atoms, and that the molecule can contain a maximum of only 3 aromatic rings, e, f, g, h, i and k, which may be identical or different, each represent hydrogen or $C_1$–$C_4$-alkyl, and R represents a $C_1$–$C_{18}$-alkyl radical, a $C_2$–$C_{18}$-alkenyl radical, a $C_6$–$C_{14}$-aryl radical or a $C_7$–$C_{20}$-aralkyl radical, it being possible for these to be substituted by alkoxy or halogen.

Examples of the solvents containing phosphorus which can be used in the process according to the invention are: 1-oxo-1-methyl-3-phospholine, 1-oxo-1-ethyl-3-phospholine, 1-oxo-1-benzyl-3-phospholine, 1-oxo-1-phenyl-3-phospholine, 1-oxo-1,3-dimethyl-3-phospholine, 1-oxo-1-benzyl-3-methyl-3-phospholine, 1-oxo-1-phenyl-3-methyl-3-phospholine, 1-oxo-1-methyl-3-chloro-3-phospholine, 1-oxo-1-benzyl-3-chloro-3-phospholine, 1-oxo-1-phenyl-3-chloro-3-phospholine, 1-oxo-1-phenyl-3,4-dimethyl-3-phospholine, 1-oxo-1-methyl-2-phospholine, 1-oxo-1-ethyl-2-phospholine, 1-oxo-1-benzyl-2-phospholine, 1-oxo-1-phenyl-2-phospholine, 1-oxo-1-phenyl-3,4-dimethyl-2-phospholine, 1-oxo-1-methyl-phospholane, 1-oxo-1-ethyl-phospholane, 1-oxo-1-benzyl-phospholane, 1-oxo-1-phenyl-phospholane, 1-oxo-1,3-dimethyl-phospholane, 1-oxo-1-benzyl-3-methyl-phospholane, 1-oxo-1-ethyl-3-phospholane, 1-oxo-1-phenyl-3-methyl-phospholane, 1-oxo-1-phenyl-3-isohexyl-phospholane, 1-oxo-1,2,2,3,4,4-hexamethyl-phosphetane, 1-oxo-1-benzyl-2,2,3,4,4-pentamethyl-phosphetane, 1-oxo-1-phenyl-2,2,3,3,4-pentamethyl-phosphetane, 1-oxo-1-phenyl-2,2,3,3-tetramethyl-phosphetane and 1-oxo-1-phenyl-2,2,3-trimethyl-phosphetane. Of course, mixtures of two or more of these solvents can be used.

The process according to the invention is carried out in the presence of salts, such as halides, cyanides, thiocyanates or azides, possible cations being alkali metals, such as lithium, sodium and potassium, and ammonium cations of the general formula

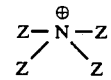

(VIII)

wherein the radicals Z, which may be identical or different, each represent optionally substituted alkyl, aralkyl or aryl, or two adjacent radicals Z, together with the nitrogen atom, form a heterocyclic ring.

Ammonium cations are preferred in which Z stands for $C_1$–$C_{18}$-alkyl(such as methyl, ethyl, propyl, butyl, hexyl, dodecyl and octadecyl); benzyl which is optionally substituted by $C_1-C_4$-alkyl, methoxy or halogen; or phenyl which is optionally substituted by $C_1-C_4$-alkyl, methoxy or halogen. Ammonium cations in which two radicals Z, together with the adjacent nitrogen atom, form a 5- or 6-membered heterocyclic ring, such as pyrrolidine, piperidine or morpholine, are also preferred.

The following may be mentioned as examples of particularly preferred salts which are to be used according to the invention: tetramethylammonium chloride, tetraethylammonium chloride, tetrabutylammonium chloride, tetrabutylammonium bromide, tetrabutylammonium iodide, methylbutylpiperidinium chloride, triethylbenzylammonium chloride, benzyldodecyldimethylammonium chloride, sodium chloride and sodium bromide.

The amount of salt used is usually 0.1 to 1.5 moles, per mole of the carboxylic acid ester (I) to be decarbalkoxylated. However, a still greater excess is not harmful.

Surprisingly, the presence of water is not necessary during the reaction, but an at least equimolar amount of water must be added to the reaction mixture after the reaction has ended in order to protonate the anion formed, thus:

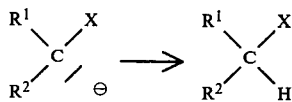

It is also possible, of course, to have water present from the start, appropriately in an amount of 1 to 3 moles per mole of the carboxylic acid ester (I) employed. Thus, about 1 to 3 moles of water are present at some time before separation of the decarboxylated product.

If the solvent containing phosphorus used is solid, it can be melted before adding the carboxylic acid ester (I) to be decarbalkoxylated; however, it can also be appropriate additionally to add an inert organic diluent, such as, for example, toluene, xylene, chlorobenzene, dichlorobenzene, diethylene glycol dimethyl ether, diethylene glycol diethyl ether, sulpholane or hexamethylphosphoric acid triamide.

When solvents containing phosphorus according to the invention are used, in most cases the conversion is quantitative after a relatively short time. The course of the reaction can be followed by the evolution of $CO_2$.

The process according to the invention is generally carried out by heating the carboxylic acid esters of the general formula (I), together with one of the solvents, containing phosphorus, of the general formula (IV), (V), (VI) or (VII) indicated above, or a mixture of any of these, optionally in an inert organic solvent in the presence of salts of the general formula (III), to 100°–250°, preferably about 140°–200° C. The optimum reaction temperature can be determined individually for each of the carboxylic acid esters to be decarbalkoxylated by establishing at which temperature the evolution of $CO_2$ begins. About 100–1000 g of solvent containing phosphorus are employed per mole of carboxylic acid ester to be decarbalkoxylated.

Working up can be carried out in the customary manner by pouring the reaction mixture, after cooling, into water and extracting with an organic solvent such as petroleum ether, benzine, benzene or toluene. The solvent containing phosphorus may be recovered from the aqueous phase by fractional distillation. The organic phase is also worked up by fractional distillation.

In a preferred process variant, the reaction product is directly distilled out of the reaction solution, it being necessary to ensure that the difference between the boiling point of the solvent containing phosphorus and that of the desired carboxylic acid ester of the general formula (II) is sufficiently great. The distillation residue can be employed again or the solvent containing phosphorus can be recovered by distillation. With the aid of the process according to the invention it is possible, for example, to prepare 2,2-dimethyl-3-(2',2'-dichlorovinyl)-cyclopropane-1-carboxylic acid ester from 2,2-dimethyl-3-(2',2'-dichlorovinyl)-cyclopropane-1,1-dicarboxylic acid ester with quantitative conversion and in 90% yield. The former is used as an intermediate for valuable highly active insecticides (see German Offenlegungsschriften (German Published Specifications) Nos. 2,326,077, 2,418,950, 2,436,178 and 2,439,177).

The process of the present invention is illustrated by the following preparative examples:

EXAMPLE 1

30 g (0.1 mol) of 2,2-dimethyl-3-(2',2'-dichlorovinyl)-cyclopropane-1,1-dicarboxylic acid diethyl ester, 50 ml of 1-oxo-1-methyl-phospholine, 6 g of sodium chloride and 4 ml of water were heated to 175° C. for 9 hours. The mixture was then cooled, poured into 150 ml of water and extracted with petroleum ether. After drying with $MgSO_4$, the mixture was fractionally distilled. 21.3 g (=90% of theory) of 2,2-dimethyl-3-(2',2'-dichlorovinyl)-cyclopropane-1-carboxylic acid ethyl ester of boiling point 65°–75° C./0.1 mm Hg were obtained. 49.7 g of 1-oxo-1-methyl-phospholine of boiling point 75°–77° C./0.15 mm Hg were recovered by fractional distillation of the aqueous phase.

COMPARISON EXAMPLE

In comparison with this, the reaction was carried out in the presence of DMSO according to the following process of German Offenlegungsschrift (German Published Specification) No. 2,536,145:

A mixture of 2,2-dimethyl-3-(2',2'-dichlorovinyl)-cyclopropane-1,1-dicarboxylic acid diethyl ester (5 g), sodium chloride (0.95 g), dimethylsulphoxide (12 ml) and water (0.6 ml) was heated to 175° C. under a nitrogen atmosphere and kept at this temperature for 9 hours. At the end of this period, the mixture was cooled to room temperature and poured into water (50 ml). The mixture was extracted with petroleum ether (boiling point 60° to 80°) and the extracts were dried over anhydrous magnesium sulphate. After removing the solvent by evaporation under reduced pressure, the residual oil was purified by distillation, 2,2-dimethyl-3-(2',2'-dichlorovinyl)-cyclopropane-1-carboxylic acid ethyl ester being obtained as a colorless liquid (boiling point 102° C./13.3 mm Hg) in a yield of 15–20% of theory.

EXAMPLE 2

30 g (0.1 mol) of 2,2-dimethyl-3-(2',2'-dichlorovinyl)-cyclopropane-1,1-dicarboxylic acid diethyl ester, 50 ml of 1-oxo-1-ethyl-3-methyl-3-phospholine, 6 g of sodium chloride and 4 ml of water were heated to 175° C. for 10 hours. After cooling, 3 ml of ethanol were distilled off; 18.3 g (77% of theory) of 2,2-dimethyl-3-(2',2'- dichlorovinyl)-cyclopropane-1-carboxylic acid ethyl ester of boiling point 72°–76° C./0.3 mm Hg were then directly distilled out of the reaction mixture through a small column. The residue consisted of crude 1-oxo-1-ethyl-3-methyl-3-phospholine and could be employed again for decarbalkoxylation. When it was worked up by distillation, 46 ml of 1-oxo-1-ethyl-3-methyl-3-phospholine of boiling point 108°–112° C./0.3 mm Hg were recovered.

EXAMPLE 3

23 g (0.1 mol) of 2,2-dimethyl-3-methylthio-cyclopropane-1,1-dicarboxylic acid dimethyl ester (prepared according to J. Chem. Soc., Chem. Comm. 1972 (7), 375) were dissolved in 25 ml of 1-oxo-1-methylphospholine and 2 ml of water and the solution was heated to 180° C. with 8 g of sodium bromide for 12 hours. The mixture was then cooled, poured into water, extracted by shaking with toluene and distilled. 12 g (=69% of theory) of 2,2-dimethyl-3-methylthiocyclopropane-1-carboxylic acid methyl ester of boiling point 75° C./3 mm Hg are obtained.

$C_8H_{14}O_2S$: calculated: C 55.2%, H 8.0%; found: C 55.4%, H 8.0%.

EXAMPLE 4

Analogously to Example 3, 3-cyano-2,2-dimethyl-cyclopropane-1-carboxylic acid ethyl ester of boiling point 95° C./3 mm Hg was obtained from 3-cyano-2,2-dimethyl-cyclopropane-1,1-dicarboxylic acid diethyl ester (prepared according to J. Chem. Soc., Chem. Comm. 1972 (7) 375).

EXAMPLE 5

In a similar manner to Example 3, 2,2-dimethyl-3-phenylthio-cyclopropane-1-carboxylic acid ethyl ester of boiling point 93° C./0.001 mm Hg was obtained from 2,2-dimethyl-3-phenylthio-cyclopropane-1,1-dicarboxylic acid diethyl ester (prepared according to J. Chem. Soc., Chem. Comm. 1972 (7), 375).

EXAMPLE 6

67.8 g (0.3 mol) of 2,2-dimethyl-3-propynyl-malonic acid diethyl ester (prepared according to J. Biol. Chem., Volume 175, page 771; 1948), 50 ml of 1-oxo-1-ethyl-phospholine, 20 g of tetraethylammonium chloride and 10 g of water were heated to 180° C. for 12 hours. After cooling, the mixture was fractionally distilled under reduced pressure. The first runnings of 12 g essentially consisted of ethanol. The main runnings had a boiling point 60°–70° C./25 mm Hg and consisted of 34.5 g of 2,2-dimethyl-3-butyne-1-carboxylic acid ethyl ester (yield: 75% of theory).

COMPARISON EXAMPLE 113 g (0.5 mol) of 2,2-dimethyl-3-propynyl-malonic acid diethyl ester, 250 ml of dimethylsulphoxide, 36 g of water and 35 g of sodium chloride were heated to 180° C. for 12 hours. The evolution of $CO_2$ started at 165° C. After cooling, the mixture was poured into 1,000 ml of ice-water and extracted with petroleum ether. After separating off the petroleum ether phase, this was dried with magnesium sulphate and then fractionally distilled. 19 g (24.7% of theory) of 2,2-dimethyl-3-butyne-1-carboxylic acid ethyl ester of boiling point 65°–68° C./15 mm Hg were obtained.

EXAMPLE 7

98.5 g (0.5 mol) of diisopropyl-cyanoacetic acid ethyl ester (prepared according to J. Chem. Soc., 1930, page 2,758), 300 ml of 1-oxo-1-methyl-phospholine, 31 g of sodium chloride and 22 g of water were heated to 160°–170° C. for 9 hours. After cooling, the mixture was diluted with 1,000 ml of water and extracted by shaking four times with 150 ml of petroleum ether each time. The combined petroleum ether phases were washed twice with 200 ml of water each time and dried with $Na_2SO_4$ and the petroleum ether was distilled off under normal pressure. The residual crude product was then purified by vacuum distillation. 53.2 g (85% of theory) of diisopropyl-acetonitrile of boiling point 60° C./14 mm Hg were obtained. Refractive index $n_D^{20}=1.4190$.

EXAMPLE 8

16.9 g (0.069 mol) of diisopropyl-malonic acid diethyl ester (prepared according to J. Chem. Soc., 1931, page 2,336), 25 ml of 1-oxo-1-methyl-phospholine, 4.5 g of sodium chloride and 3.2 g of water were heated to 160°–170° C. for 14 hours. After cooling, the mixture was diluted with 200 ml of water and extracted by shaking four times with a total of 200 ml of petroleum ether and the petroleum ether phase was washed twice with 50 ml of water each time and dried with sodium sulphate. After distilling off the petroleum ether under normal pressure, the crude product was fractionally distilled in vacuo. 8.1 g (68% of theory) of diisopropylacetic acid ethyl ester of boiling point 70°–72°/22 mm Hg were obtained (refractive index $n_D^{22}=1.4160$).

EXAMPLE 9

43.2 g (0.3 mol) of methyl-acetoacetic acid ethyl ester, 60 ml of 1-oxo-1-methyl-phospholine, 20 g of sodium chloride and 12 g of water were heated to 170°–180° C. in a column with a column head. The mixture of ethanol and butanone formed was continuously distilled off over the column head. 33.5 g of distillate were obtained which, according to analysis by gas chromatography, contained 19.9 g of butanone. This corresponds to a yield of 92% of theory.

EXAMPLE 10

56.4 g (0.3 mol) of diethylmalonic acid dimethyl ester, 60 ml of 1-oxo-1-methyl-phospholine, 20 g of sodium chloride and 12 g of water were heated to 175° C. for 12 hours. After cooling, the mixture was distilled in vacuo. 59.6 g of a distillate were obtained which consisted of water, methanol and diethylacetic acid methyl ester. The distillate was diluted with 100 ml of water and extracted three times with 150 ml of methylene chloride and the combined organic phases were dried with sodium sulphate and fractionally distilled under normal pressure. Yield: 38.5 g (89% of theory) of diethylacetic acid methyl ester. Boiling point 122°–134° C./760 mm Hg.

It will be appreciated that the instant specification and examples are set forth by way of illustration and not limitation, and that various modifications and changes may be made without departing from the spirit and scope of the present invention.

What is claimed is:

1. A process for the decarbalkoxylation of a carboxylic acid ester of the formula

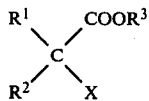

in which

X is COOR$^4$, COR$^5$ or CN,

R$^1$ and R$^2$ each independently is hydrogen, alkyl, alkenyl, alkynyl, aryl or aralkyl or, R$^1$ and R$^2$, together with the adjacent carbon atom, form a cycloaliphatic ring which is optionally substituted by CN, alkyl, alkenyl, aryl, aralkyl, thioalkyl or thioaryl, the substituents of the cycloaliphatic ring optionally being substituted by halogen, R$^3$ and R$^4$ each independently is alkyl, and R$^5$ is alkyl, alkenyl, aryl or aralkyl, or R$^4$ or R$^5$ forms a ring with R$^2$ and the intermediate atoms, to give a product of the formula

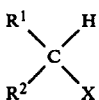

which comprises heating the carboxylic acid ester at about 100°–250° C. in the presence of a solvent containing phosphorus and in the presence of about 0.1 to 1.5 times the molar amount of a salt, the solvent containing phosphorus being selected from the group consisting of at least one phospholine oxide or phosphetane oxide of the formula

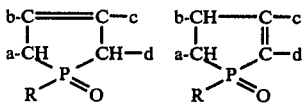

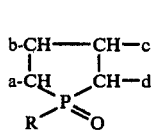

wherein a, b, c and d each independently is H, alkyl, alkenyl, aryl, aralkyl, alkoxy, Cl or Br, or are a tetramethylene radical which, together with two adjacent carbon atoms of the heterocyclic ring, form a 6-carbon atom cycloaliphatic ring, provided that if a, b, c and d are aliphatic, they contain a total of not more than 6 carbon atoms and that the solvent contains not more than 3 aromatic rings, e, f, g, h, i and k each independently is H or C$_1$–C$_4$-alkyl, and R is C$_1$–C$_{18}$-alkyl, C$_2$–C$_{18}$-alkenyl, C$_6$–C$_{14}$-aryl or C$_7$–C$_{20}$-aralkyl, any of which is optionally substituted by alkoxy or halogen, and the salt comprising a halide, cyanide, thiocyanate or azide, and then separating the ester formed.

2. A process according to claim 1, in which

R$^1$ and R$^2$ each independently is H, or C$_1$–C$_{18}$-alkyl, C$_2$–C$_{18}$-alkenyl, C$_2$–C$_{18}$-alkynyl, C$_6$–C$_{14}$-aryl or C$_7$–C$_{20}$-aralkyl, optionally substituted by fluorine, chlorine, bromine, iodine or cyano, at least one of them being branched in α-position, or R$^1$ and R$^2$, together with the adjacent carbon atom, form a cyclopropane ring optionally substituted by cyano or by C$_1$–C$_{18}$-alkyl, C$_2$–C$_{18}$-alkenyl, C$_6$–C$_{14}$-aryl, C$_7$–C$_{20}$-aralkyl, alkylthio or arylthio, any of which in turn is optionally substituted by fluorine, chlorine, bromine or iodine, R$^3$ is C$_1$–C$_4$-alkyl, R$^4$ is C$_1$–C$_4$-alkyl or, together with R$^2$, forms a lactone with 3–6 carbon atoms, and R$^5$ is C$_1$–C$_{18}$-alkyl, C$_2$–C$_{18}$-alkylene, C$_6$–C$_{14}$-aryl or C$_7$–C$_{20}$-aralkyl, optionally substituted by halogen or R$^5$, together with R$^2$, forms a cyclic ketone with 3–7 carbon atoms.

3. A process according to claim 1, in which the salt has a cation selected from alkali metals and ammonium cations of the formula

wherein each Z independently is optionally substituted alkyl, aralkyl or aryl, or two adjacent Z radicals, together with the nitrogen atom, form a heterocyclic ring.

4. A process according to claim 3, in which the cation is lithium, sodium or potassium or an ammonium cation of the formula shown wherein Z is C$_1$–C$_{18}$ alkyl, benzyl optionally substituted by C$_1$–C$_4$ alkyl, methoxy or halogen, or phenyl optionally substituted by C$_1$–C$_4$ alkyl, methoxy or halogen, or two adjacent Z radicals, together with the nitrogen atom, form a 5 or 6- membered heterocyclic ring.

5. A process according to claim 1, in which the salt comprises sodium chloride.

6. A process according to claim 1, in which water is substantially absent during the reaction and is added in an at least equimolar amount in order to protonate the anion R$^1$R$^2$CX$^\ominus$ which is produced in the reaction.

7. A process according to claim 1, in which about 1 to 3 moles of water per mole of ester are present at the start of the reaction.

8. A process according to claim 2, in which the solvent containing phosphorus is present in about 100 to 1000 g per mole of ester, the salt is sodium chloride, the reaction is carried out at about 140° to 200° C. and about 1 to 3 moles of water per mole of ester are present at some time before separation of the decarboxylated product.

* * * * *